United States Patent
Höglund (10) Patent No.: US 12,036,564 B2
(45) Date of Patent: Jul. 16, 2024

(54) EXCHANGEABLE SEPARATION INSERT AND MODULAR CENTRIFUGAL SEPARATOR AND METHOD

(71) Applicant: Alfa Laval Corporate AB, Lund (SE)

(72) Inventor: Kasper Höglund, Rönninge (SE)

(73) Assignee: ALFA LAVAL CORPORATE AB, Lund (SE)

( * ) Notice: Subject to any disclaimer, the term of this patent is extended or adjusted under 35 U.S.C. 154(b) by 664 days.

(21) Appl. No.: 17/296,404

(22) PCT Filed: Dec. 9, 2019

(86) PCT No.: PCT/EP2019/084143
§ 371 (c)(1),
(2) Date: May 24, 2021

(87) PCT Pub. No.: WO2020/120361
PCT Pub. Date: Jun. 18, 2020

(65) Prior Publication Data
US 2022/0023886 A1     Jan. 27, 2022

(30) Foreign Application Priority Data

Dec. 10, 2018   (EP) .................................... 18211240

(51) Int. Cl.
*B04B 1/08*     (2006.01)
*B04B 5/04*     (2006.01)
(Continued)

(52) U.S. Cl.
CPC .............. *B04B 1/08* (2013.01); *B04B 5/0442* (2013.01); *B04B 7/12* (2013.01); *C12M 33/10* (2013.01); *C12M 47/02* (2013.01)

(58) Field of Classification Search
CPC ........... B04B 1/08; B04B 5/0442; B04B 7/12; B04B 7/08; C12M 33/10; C12M 47/02
See application file for complete search history.

(56) References Cited

U.S. PATENT DOCUMENTS

| | | |
|---|---|---|
| 2,104,683 A | 1/1938 | Rosen et al. |
| 3,602,425 A | 8/1971 | Schmidt |

(Continued)

FOREIGN PATENT DOCUMENTS

| | | |
|---|---|---|
| CN | 2551250 Y | 5/2003 |
| CN | 104841577 A | 8/2015 |

(Continued)

OTHER PUBLICATIONS

English translation of the Japanese Office Action and Search Report for Japanese Application No. 2021-532946, dated Apr. 25, 2022.

(Continued)

*Primary Examiner* — Walter D. Griffin
*Assistant Examiner* — Shuyi S. Liu
(74) *Attorney, Agent, or Firm* — Birch, Stewart, Kolasch & Birch, LLP (57) ABSTRACT

An exchangeable separation insert, a modular centrifugal separator, and a method are disclosed. The exchangeable separation insert includes a rotor casing rotatable about an axis of rotation and a first stationary portion. The exchangeable separation insert includes a ring member which extends concentrically with the axis. The ring member is axially displaceable between a first position, in which the ring member abuts radially against the rotor casing and abuts radially, against the first stationary portion, and a second position, in which the ring member abuts radially against the rotor casing only, or against the first stationary portion only.

29 Claims, 5 Drawing Sheets

(51) Int. Cl.
*B04B 7/12* (2006.01)
*C12M 1/00* (2006.01)
*C12M 1/26* (2006.01)

(56) References Cited

U.S. PATENT DOCUMENTS

| | | |
|---|---|---|
| 5,637,217 A | 6/1997 | Herman et al. |
| 6,439,577 B2 | 8/2002 | Jorgensen et al. |
| 6,709,377 B1 | 3/2004 | Rochat |
| 6,821,319 B1 | 11/2004 | Moberg et al. |
| 7,037,428 B1 | 5/2006 | Robinson et al. |
| 2009/0280974 A1 | 11/2009 | Klintentedt |
| 2011/0319248 A1 | 12/2011 | Starbard |
| 2016/0184836 A1 | 6/2016 | Mackel et al. |
| 2017/0189915 A1 | 7/2017 | Mackel et al. |
| 2017/0203306 A1 | 7/2017 | Penkl et al. |
| 2018/0147581 A1 | 5/2018 | Quiter et al. |
| 2018/0290152 A1 | 10/2018 | Mackel et al. |

FOREIGN PATENT DOCUMENTS

| | | |
|---|---|---|
| DE | 10 2009 053 660 B3 | 5/2011 |
| EP | 0 241 128 A1 | 10/1987 |
| EP | 3 384 993 A1 | 10/2018 |
| GB | 2523663 A | 9/2015 |
| JP | 56-133349 U | 10/1981 |
| JP | 62-254855 A | 11/1987 |
| JP | 2009-541030 A | 11/2009 |
| JP | 2017-533018 A | 11/2017 |
| JP | 2018-503513 A | 2/2018 |
| WO | WO 2008/013495 A1 | 1/2008 |
| WO | WO 2008/106409 A1 | 9/2008 |
| WO | WO 2014/000829 A1 | 1/2014 |
| WO | WO 2015/181175 A2 | 12/2015 |
| WO | WO 2015/181177 A1 | 12/2015 |
| WO | WO 2016/063111 A1 | 4/2016 |
| WO | WO 2016/120029 A1 | 8/2016 |
| WO | WO 2016/192927 A1 | 12/2016 |
| WO | WO 2018/184813 A1 | 10/2018 |

OTHER PUBLICATIONS

European Notice of Opposition dated Apr. 19, 2022 for Application No. 18211240.9 with an English translation.
English translation of Chinese Office Action and Search Report for Chinese Application No. 201980081579.X, dated Jun. 30, 2022.
International Search Report, issued in PCT/EP2019/084143, dated Feb. 11, 2020.
Written Opinion of the International Searching Authority, issued in PCT/EP2019/084143, dated Feb. 11, 2020.

EXCHANGEABLE SEPARATION INSERT AND MODULAR CENTRIFUGAL SEPARATOR AND METHOD

TECHNICAL FIELD

The invention relates to an exchangeable separation insert of a modular centrifugal separator. The invention further relates to a modular centrifugal separator. Also, the invention relates to a method of mounting an exchangeable separation insert in a modular centrifugal separator.

BACKGROUND

In the field of pharmaceuticals, biopharmaceuticals, biotechnology and thereto related fields separation of substances from a liquid mixture, such as separation of cells from a cell culture, is performed in a sterile environment. Traditionally, equipment made e.g. from stainless steel has been used, which equipment is sterilised between batches.

Lately, disposable separation equipment made for single use, i.e. for one batch or a limited number of batches, has been suggested. For instance, US 2011/0319248 discloses a single use centrifuge and WO 2015/181177 discloses a separator comprising an exchangeable inner drum.

Such disposable separation equipment is supplied to the user in a sterile manner. Thus, a sterile environment for the product in the separator may be provided without sterilisation of the separation equipment at the production facility of the user.

WO 2015/181177 discloses a separator for the centrifugal processing of a flowable product comprising a rotatable outer drum and an exchangeable inner drum arranged in the outer drum. The inner drum comprises means for clarifying the flowable product. The outer drum is driven via a drive spindle by a motor arranged below the outer drum. The inner drum extends vertically upwardly through the outer drum with fluid connections arranged at an upper end of the separator.

SUMMARY

It is an object of the invention to provide an exchangeable separation insert which is easy to handle. It is a further object of the invention to provide for easy mounting of an exchangeable separation insert in a modular centrifugal separator.

According to an aspect of the invention, at least one of the above-mentioned objects is achieved by an exchangeable separation insert of a modular centrifugal separator. The exchangeable separation insert comprises a rotor casing rotatable about an axis of rotation and having a first axial end portion and a second axial end portion, and a first stationary portion provided with a first conduit portion. The first stationary portion abuts against the rotor casing at the first axial end portion. The rotor casing delimits a separation space. The exchangeable separation insert comprises frustoconical separation discs arranged in the separation space, and the first conduit portion is fluidly connected with the separation space. The exchangeable separation insert comprises a ring member which extends concentrically with the axis of rotation at the first axial end portion, wherein the ring member is axially displaceable between a first position, in which the ring member abuts radially against the rotor casing and abuts radially against the first stationary portion, and a second position, in which the ring member abuts radially against the rotor casing only or against the first stationary portion only.

Since the exchangeable separation insert comprises the ring member, and since the ring member in the first position abuts radially against the rotor casing and abuts radially against the first stationary portion, the ring member contributes to hold the rotor casing and the first stationary portion together when the exchangeable separation insert is handled, e.g. prior to being installed in the modular centrifugal separator. More importantly, in its first position, the ring member contributes to maintaining a sterile environment within the exchangeable separation insert during handling of the exchangeable separation insert. Moreover, since the ring member in the second position abuts radially against the rotor casing only, or against the first stationary portion only, the rotor casing is released from the first stationary portion, and thus can rotate in relation to the first stationary portion. As a result, the exchangeable separation insert is easy to handle as a unit when the ring member is in its first position. Also, the axial displacement of the ring member between the first and second positions provides for an easy mounting of the exchangeable separation insert in the modular centrifugal separator.

According to a further aspect of the invention, at least one of the above-mentioned objects is achieved by a modular centrifugal separator comprising a stationary frame, a rotatable member, a drive unit for rotating the rotatable member, and an exchangeable separation insert according to any one of aspects and/or embodiments discussed herein. The rotor casing is engaged inside the rotatable member, and the first stationary portion is fixedly engaged with the stationary frame. The ring member is arranged in the second position. Since, the rotor casing is engaged in the rotatable member, and the first stationary portion is fixedly engaged with the stationary frame, the rotor casing is rotatable together with the rotatable member by the drive unit while the first stationary portion is maintained stationary. Moreover, since the ring member is arranged in its second position, the rotor casing is released from the first stationary portion thus, permitting rotation of the rotor casing engaged in the rotatable member in relation to the first stationary portion engaged with the stationary frame. Accordingly, the exchangeable separation insert is easily mountable in the modular centrifugal separator, and easily set up with a rotatable rotor casing and a fixed first stationary portion.

The modular centrifugal separator may comprise two main parts, the base unit and the exchangeable separation insert. The base unit may comprise basic components for supporting and rotating the exchangeable separation insert. The exchangeable separation insert may be configured for the actual separation of the liquid feed mixture to take place in the separation space thereof. The liquid feed mixture may flow through one fluid connection into the separation space and the separated heavy and light phases may leave the separation space via one fluid connection each. The first conduit portion may form part of one of the fluid connections.

The exchangeable separation insert may be configured for single use, i.e. for separation of one batch only or a limited number of batches of liquid feed mixture. The base unit on the other hand may be configured for repeated use with different exchangeable separation inserts, i.e. the base unit may be used for the separation of numerous batches of liquid feed mixture using different exchangeable separation inserts.

The exchangeable separation insert may be configured to form the only part of the modular centrifugal separator, which is in contact with the liquid feed mixture, and the separated heavy and light phases. Thus, the exchangeable separation insert may be provided to a user as a sterile entity. The sterile entity may include parts configured for separating the liquid feed mixture as well as conduits for the liquid feed mixture and the separated heavy and light phases. The exchangeable separation insert is mounted in the base unit by the user. Thus, the user will readily have available a centrifugal separator with a sterile environment for separation of the liquid feed mixture.

The rotatable member of the base unit may be rotatably supported in the stationary frame. The rotatable member may be supported in the stationary frame without the aid of a spindle or other kind of rotor shaft. The stationary frame is stationary in the sense that it is stationary during use of the modular centrifugal separator.

The exchangeable separation insert may further comprise a second stationary portion provided with a second conduit portion. When the exchangeable separation insert is mounted in the base unit, the rotor casing may be received in an inner space of the rotatable member. Suitably, the rotatable member may be provided with one opening at each axial end of the rotatable member for fluid connections of the exchangeable separation insert to extend therethrough.

According to embodiments, the ring member may be arranged in sealing abutment with the rotor casing and with the first stationary portion when the ring member is positioned in the first position. In this manner, the ring member may contribute to maintaining a sterile environment inside the rotor casing and the first stationary portion while the ring member is positioned in the first position.

According to embodiments, the exchangeable separation insert may comprise a first sealing member arranged between the first stationary portion and the rotor casing, wherein the first sealing member seals a transition of the first conduit portion to the rotor casing. In this manner, a mechanical hermetical seal may be provided between the first conduit portion and an inside of the rotor casing. For instance, if the first conduit portion forms part of an inlet for the liquid feed mixture, the first sealing member may provide a mechanically hermetically sealed inlet of the modular centrifugal separator. The above-mentioned abutment between the first stationary portion and the rotor casing may be provided by the first sealing member.

According to embodiments, the exchangeable separation insert may comprise a second stationary portion provided with a second conduit portion. The second stationary portion may abut against the rotor casing at the second axial end portion, and the second conduit portion may be fluidly connected with the separation space. In this manner, a further fluid connection to or from the separation space may be provided at the axial end portion of the rotor casing opposite to the first axial end portion of the rotor casing.

According to embodiments, the exchangeable separation may comprise a second sealing member arranged between the second stationary portion and the rotor casing, wherein the second sealing member seals a transition of the second conduit portion to the rotor casing. In this manner, a mechanical hermetical seal may be provided between the second conduit portion and an inside of the rotor casing. For instance, if the second conduit portion forms part of an outlet for the separated heavy phase or light phase, the second sealing member may provide a mechanically hermetically sealed outlet of the modular centrifugal separator. The above-mentioned abutment between the second stationary portion and the rotor casing may be provided by the second sealing member.

According to embodiments, the exchangeable separation insert may comprise a sleeve member. The sleeve member may be arranged in a setup position in sealing abutment with the rotor casing and the second stationary portion. The sleeve member may be removable from the setup position for permitting the rotor casing to rotate in relation to the second stationary portion. In this manner, when arranged in the setup position, the sleeve member may contribute to maintaining a sterile environment inside the rotor casing and the second stationary portion. When the rotor casing is mounted in the rotatable member of the modular centrifugal separator, the sleeve member suitably is removed from the setup position in order to allow rotation of the rotor casing in relation to the second stationary portion.

According to embodiments, the first stationary portion may be provided with a third conduit portion which is fluidly connected with the separation space. In this manner, a further fluid connection to or from the separation space may be provided at the first stationary portion of the exchangeable separation insert.

According to embodiments, the first stationary portion may comprise an outer threaded portion. In this manner, the first stationary portion may engage with the stationary frame of the modular centrifugal separator via the outer threaded portion.

According to embodiments, the rotatable member may have a first axial end and a second axial end. The rotatable member may be provided with a first opening at the first axial end. Part of the exchangeable separation insert may extend through the first opening. In this manner, for instance a fluid connection of the exchangeable separation insert may extend through the first opening.

According to embodiments, the rotatable member may be provided with a second opening at the second axial end. Part of the exchangeable separation insert may extend through the second opening. In this manner, for instance a fluid connection of the exchangeable separation insert may extend through the second opening.

According to embodiments, the rotatable member may comprise a protrusion. The ring member of the exchangeable separation insert may abut against the protrusion. In this manner, the ring member may be axially displaced from its first position to its second position when the exchangeable separation insert is mounted in the modular centrifugal separator. More specifically, as the rotor casing of the exchangeable separation insert is positioned inside the rotatable member of the stationary frame, part of the exchangeable separation insert extends through the first opening. The ring member, still in its first position, abuts against the protrusion. Thereafter, the exchangeable separation insert is moved into a final position. The ring member is displaced to its second position as the exchangeable separation insert is moved into its final position due to the protrusion abutting against the ring member.

According to embodiments, the stationary frame may comprise a housing, wherein the rotatable member is arranged inside the housing. The housing may comprise a lid provided with a third opening. In an open position of the lid, access is provided to the rotatable member for exchange of the exchangeable separation insert, and in a closed position of the lid, the third opening is configured for a fluid connection of the exchangeable separation insert to extend therethrough. In this manner, one of the fluid connections of the exchangeable separation insert may be arranged to extend through the housing for connection to equipment external of the modular centrifugal separator.

According to embodiments, the lid may be configured to engage with the second stationary portion of the exchangeable separation insert. In this manner, the second stationary portion may be fixed in relation to the housing and the stationary frame during operation of the modular centrifugal separator.

According to embodiments, in the closed position of the lid, the lid may press the second stationary portion towards the rotor casing. In this manner, it may be ensured that when the exchangeable separation insert is mounted in the modular centrifugal separator, the second stationary portion is in sealing contact with the rotor casing and thus, the exchangeable separation insert and the modular centrifugal separator are set for separating the liquid feed mixture.

According to a further aspect of the invention, there is provided a method of mounting an exchangeable insert in a modular centrifugal separator according to any one of aspects and/or embodiments discussed herein, comprising steps of:
- providing an exchangeable separation insert according to any one of aspects and/or embodiments discussed herein,
- inserting the exchangeable separation insert into the rotatable member to a position in which the ring member abuts against a protrusion within the rotatable member,
- moving the exchangeable insert in an axial direction of the rotatable member further into the rotatable member, thus pushing the ring member from its first position to its second position.

Since in the step of moving the exchangeable separation insert in an axial direction of the rotatable member the ring member is pushed from its first position to its second position, the rotor casing of the exchangeable separation insert is released from the first stationary portion. Accordingly, an easy mounting of the exchangeable separation insert in the modular centrifugal separator is provided.

Further features of, and advantages with, the invention will become apparent when studying the appended claims and the following detailed description.

BRIEF DESCRIPTION OF THE DRAWINGS

Various aspects and/or embodiments of the invention, including its particular features and advantages, will be readily understood from the example embodiments discussed in the following detailed description and the accompanying drawings, in which:

FIG. 1 schematically illustrates a modular centrifugal separator according to embodiments, FIG. 2 schematically illustrates a cross-section through an exchangeable separation insert according to embodiments, FIGS. 2a and 2b schematically illustrate cross sections through part of a first axial end portion of a rotor casing and part of a first stationary portion of an exchangeable separation insert, FIG. 3 schematically illustrates a cross section through a base unit of a modular centrifugal separator, FIG. 4 schematically illustrates a cross section through a portion of a modular centrifugal separator.

DETAILED DESCRIPTION

Aspects and/or embodiments of the invention will now be described more fully. Like numbers refer to like elements throughout. Well-known functions or constructions will not necessarily be described in detail for brevity and/or clarity.

Figure 1:
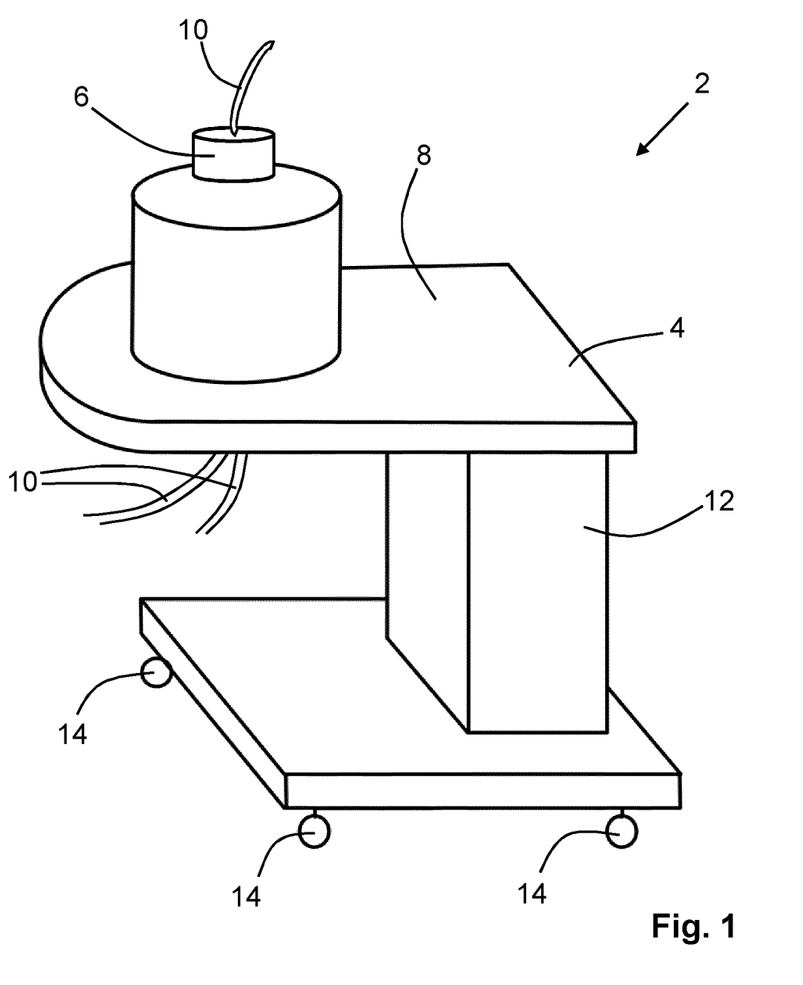

FIG. 1 schematically illustrates a modular centrifugal separator 2 according to embodiments. The modular centrifugal separator 2 comprises a base unit 4 and an exchangeable separation insert 6. The modular centrifugal separator 2 may be configured for use in the field of pharmaceuticals, biopharmaceuticals, and/or biotechnology. The modular centrifugal separator 2 may form part of a set-up in a plant for the production of cells, such as CHO cells (Chinese Hamster Ovary cells) or other matter resulting from processes in the biotech industry.

The modular centrifugal separator 2 is configured for separating a liquid feed mixture into a heavy phase and light phase. For instance, the liquid feed mixture may be formed by a fermentation broth including a cell culture, the heavy phase may comprise the cells separated from the main part of the fermentation broth. The light phase may be formed by main part the fermentation broth without the cells or with only a minimum rest amount of cells.

The modular centrifugal separator 2 is modular in the sense that it comprises the base unit 4 and the exchangeable separation insert 6. The exchangeable separation insert 6 is exchanged for each new batch of liquid feed mixture, which is to be separated. Alternatively, the exchangeable separation insert 6 may be exchanged for each new type of liquid feed mixture, which is to be separated, i.e. subsequent batches containing same type of liquid feed mixtures may be separated with the same exchangeable separation insert 6.

During use of the modular centrifugal separator 2, the liquid feed mixture, the heavy phase, and the light phase only come into contact with the exchangeable separation insert 6 of the modular centrifugal separator. Naturally, conduits in the form of tubes 10 configured for conducting the liquid feed mixture to the exchangeable separation insert 6 and for conducting the heavy phase and the light phase from the exchangeable separation insert 6 also come into contact with the liquid feed mixture and the heavy and light phases. The tubes 10 may form part of the exchangeable separation insert 6. The base unit 4 does not come into contact with the liquid feed mixture or any of the heavy and light phases.

The exchangeable separation insert 6 is further discussed below with reference to FIGS. 2-2b, and 4.

The base unit 4 comprises components for supporting and rotating the exchangeable separation insert. Thus, the base unit 4 comprises inter alia a stationary frame 8, a rotatable member, and a drive unit for rotating the rotatable member. Accordingly, also the modular centrifugal separator 2 comprises a stationary frame 8, a rotatable member, and a drive unit for rotating the rotatable member. The stationary frame 8 comprises a vertical member 12. Part of the drive unit may be arranged in the vertical member 12.

The stationary frame 8 is stationary during use of the modular centrifugal separator. However, the base unit 4 as such may be movable, e.g. in order to be positioned at different locations at a production facility of the user. For this purpose, the stationary frame 8 may be provided with wheels 14.

The base unit 4 is further discussed below with reference to FIG. 3.

Figure 2:
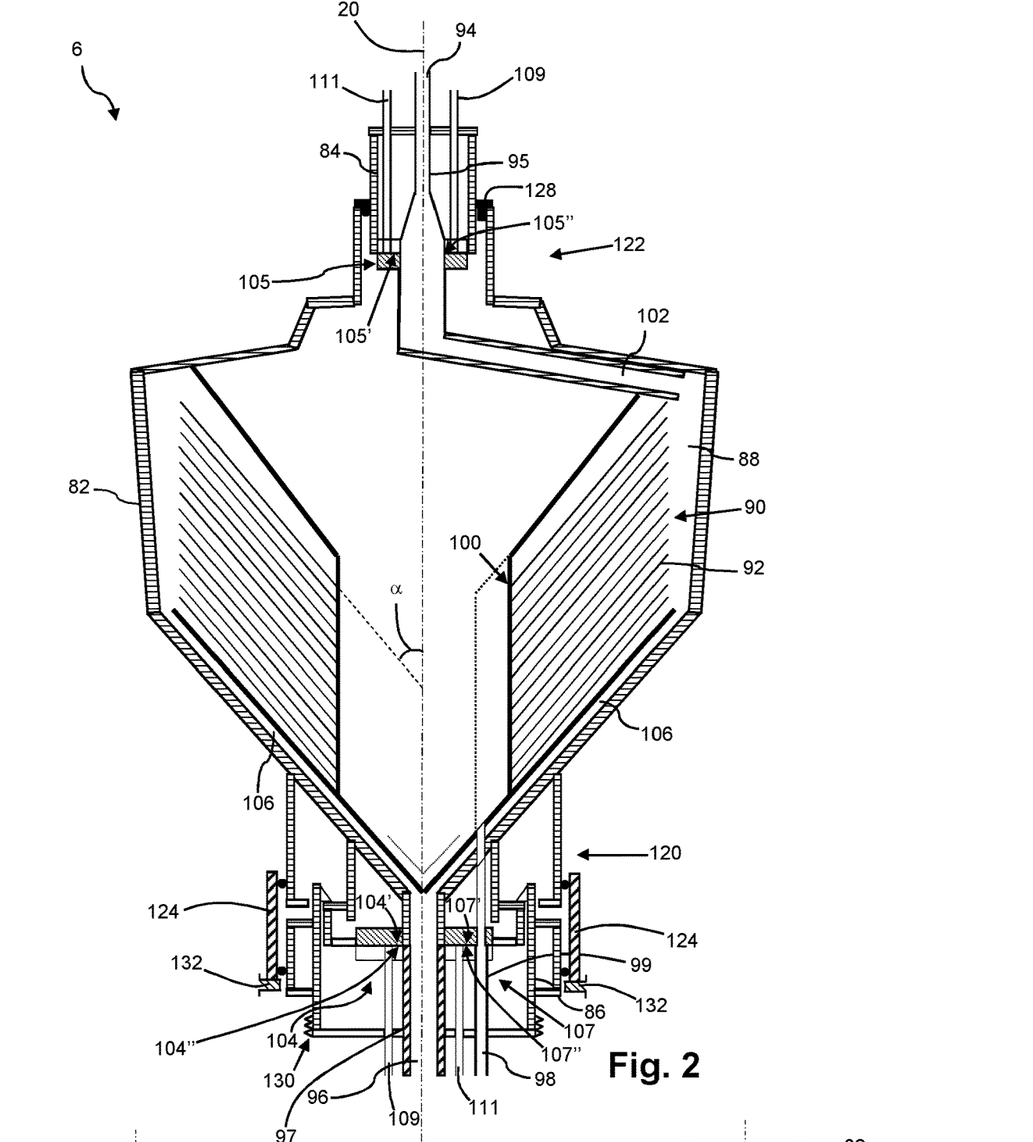

FIG. 2 schematically illustrates a cross-section through an exchangeable separation insert 6 according to embodiments. The exchangeable separation insert 6 may form part of a modular centrifugal separator, such as the modular centrifugal separator 2 discussed above in connection with FIG. 1 and below with reference to FIGS. 3 and 4. Accordingly, the exchangeable separation insert 6 may be configured for part of it to be arranged inside an inner space 26 of a rotatable member 16 as further discussed below in connection with FIG. 3.

The exchangeable separation insert 6 comprises a rotor casing 82, a first stationary portion 86 and a second stationary portion 84. The rotor casing 82 is rotatable about an axis 20 of rotation. The rotor casing 82 has a first axial end portion 120 and a second axial end portion 122. The rotor casing 82 is arranged between the first stationary portion 86 and the second stationary portion 84. During operation of the modular centrifugal separator, the first stationary portion 86 is arranged at a lower axial end of the exchangeable separation insert 6, whereas the second stationary portion 84 is arranged at an upper axial end of the exchangeable separation insert 6.

The rotor casing 82 delimits a separation space 88 therein. The exchangeable separation insert 6 comprises a stack 90 of frustoconical separation discs 92 arranged in the separation space 88. The separation discs 92 in the stack 90 are arranged with an imaginary apex at the first stationary portion 86, and/or pointing towards the first stationary portion 86. The stack 90 may comprise at least 50 separation discs 92, such as at least 100 separation discs 92, such as at least 150 separation discs 92. Mentioned as an example, a separation disc 92 may have an outer diameter within a range of 160-400 mm, an inner diameter within a range of 60-100 mm, and an angle α between the axis 20 of rotation and an inner surface of the disc 92 within a range of 35-40 degrees. For clarity reasons, only a few discs 92 are shown in FIG. 2.

The exchangeable separation insert 6 comprises a first fluid connection 96 arranged at the first stationary portion 86. A first conduit portion 97 forms part of the first fluid connection 96.

The first conduit portion 97 is fluidly connected with the separation space 88. The first conduit portion 97 of the first fluid connection 96 extends through the first stationary portion 86. The exchangeable separation insert 6 comprises a second fluid connection 94 arranged at the second stationary portion 84. A second conduit portion 95 forms part of the second fluid connection 94. The second conduit portion 95 is fluidly connected with the separation space 88. The second conduit portion 95 of the second fluid connection 94 extends through the second stationary portion 84. In these embodiments, the exchangeable separation insert 6 comprises a third fluid connection 98 arranged at the first stationary portion 86. A third conduit portion 99 forms part of the third fluid connection 98. The third conduit portion 99 is fluidly connected with the separation space 88. The third conduit portion 99 of the third fluid connection 98 extends through the first stationary portion 86. Accordingly, the first stationary portion 86 is provided with the third conduit portion 99 which is fluidly connected with the separation space 88.

In these embodiments, the first fluid connection 96 is configured for conducting the liquid feed mixture to the rotor casing 82, the second fluid connection 94 is configured for conducting the heavy phase from the rotor casing 82, and the third fluid connection 98 is configured for conducting the light phase from the rotor casing 82. From the first fluid connection 96, the liquid feed mixture flows into the separation space 88 on the axis 20 of rotation. The liquid feed mixture is distributed from the axis 20 of rotation to an outer periphery of the separation space 88. The separated light phase flows towards the axis 20 of rotation and leaves the separation space 88 at a radial position between the axis 20 of rotation and the radially inner edges 100 of the separation discs 92.

Inside the rotor casing 82 there is arranged one or more outlet conduits 102 for the separated heavy phase from the separation space 88. The one or more outlet conduits 102 extend from a radially outer portion of the separation space 88 towards the axis 20 of rotation. The one or more outlet conduits 102 may each comprise a tube. Depending on the number of outlet conduits 102 and e.g. the density and/or viscosity of the heavy phase, each tube may have an inner diameter within a range of 2-10 mm. In this example, there is provided a single outlet conduit 102. However, there may be at least two such outlet conduits, such as at least three or such as at least five outlet conduits, evenly distributed over at the circumference of the rotor casing 82. The outlet conduit 102 has a conduit inlet arranged at the radially outer portion and a conduit outlet at a radially inner portion. The outlet conduit 102 is arranged at an axially upper portion of the separation space 88.

The first stationary portion 86 abuts against the rotor casing 82 at the first axial end portion 120. The second stationary portion 84 abuts against the rotor casing 82 at the second axial end portion 122. Seals are provided between the respective first and second stationary portions 86, 84 and the rotor casing 82. The seals may form part of the stationary portions 86, 84 and/or of the rotor casing 82. In these embodiments, each of the seals comprises rotating sealing surfaces forming part of the rotor casing 82 and stationary sealing surfaces forming part of the stationary portions 86, 84. At the seals, the first and second stationary portions 86, 84, respectively, abut against the rotor casing 82.

In the illustrated embodiments, the exchangeable separation insert 6 comprises a first sealing member 104 arranged between the first stationary portion 86 and the rotor casing 82. The first sealing member 104 seals a transition of the first conduit portion 97 to the rotor casing 82. Thus, a mechanical hermetical seal is provided between the first conduit portion 97 and an inside of the rotor casing 82, such as the separation space 88.

According to the illustrate embodiments, the first sealing member 104 is fixedly arranged in the first stationary portion 86 and comprises a first annular sealing surface 104' abutting against a first opposite sealing surface 104" arranged at the rotor casing 82. In this manner, a mechanical hermetical seal is provided at an interface between the first annular sealing surface 104' and the first opposite sealing surface 104". During use of the modular centrifugal separator, the first opposite sealing surface 104" rotates with the rotor casing 82.

In the illustrated embodiments, the exchangeable separation 6 comprises a second sealing member 105 arranged between the second stationary portion 84 and the rotor casing 82. The second sealing member 105 seals a transition of the second conduit portion 95 to the rotor casing 82. Thus, a mechanical hermetical seal is provided between the second conduit portion 95 and an inside of the rotor casing 82, such as the separation space 88.

According to the illustrated embodiments, the second sealing member 105 is fixedly arranged in the second stationary portion 84 and comprises a second annular sealing surface 105' abutting against a second opposite sealing surface 105" arranged at the rotor casing 82. In this manner, a mechanical hermetical seal is provided at an interface between the second annular sealing surface 105' and the second opposite sealing surface 105". During use of the modular centrifugal separator, the second opposite sealing surface 105" rotates with the rotor casing 82.

In the illustrated embodiments, the exchangeable separation insert 6 comprises a third sealing member 107 arranged between the first stationary portion 86 and the rotor casing 82, wherein the third sealing member 107 seals a transition of the third conduit portion 99 to the rotor casing 82. Thus, a mechanical hermetical seal is provided between the third conduit portion 99 and an inside of the rotor casing 82, such as the separation space 88.

In these embodiments, the third sealing member 107 is arranged concentrically with the first sealing member 104.

According to the illustrated embodiments, the third sealing member 107 is fixedly arranged in the first stationary portion 86 and comprises a third annular sealing surface 107' abutting against a third opposite sealing surface 107" arranged at the rotor casing 82. Thus, a mechanical hermetical seal is provided between the third conduit portion 99 and an inside of the rotor casing 82, such as the separation space 88.

The sealing members 104, 105, 107 may be provided with fluid inlets 109 and fluid outlets 111 for supplying and withdrawing a fluid, such as a cooling liquid. Thus, the sealing members 104, 105, 107 may be cooled. In FIG. 2, one fluid inlet 109 and one fluid outlet 111 is shown at the sealing members 104, 105, 107. However, further fluid inlets and outlets may be provided at the sealing members 104, 105, 107.

The sealing members 104, 105, 107, form mechanical seals between the stationary portions 86, 84 and the rotor casing 82. Thus, the exchangeable separation insert 6 is provided with mechanically hermetically sealed inlet and outlets. More specifically, a fluid connection between the outlet conduit 102 arranged inside the rotor casing 82 and the second conduit portion 95 arranged in the second stationary portion 84 is mechanically hermetically sealed. Similarly, a fluid connection between the first conduit portion 97 arranged in the first stationary portion 86 and the separation space 88 inside the rotor casing 82 is mechanically hermetically sealed. Also, a fluid connection between the separation space 88 inside the rotor casing 82 and the third conduit portion 99 arranged in the first stationary portion 86 is mechanically hermetically sealed.

It is remarked that a mechanical hermetical seal forms a completely different interface between rotating and stationary parts of the centrifugal separator than a hydraulic seal comprising e.g. a paring disc arranged inside a paring chamber. A mechanical hermetical seal includes an abutment between part of the rotatable rotor casing and a stationary portion.

A hydraulic seal does not include an abutment between the rotating and stationary parts of a centrifugal separator.

The first, second, and third fluid connections 96, 94, 98 may comprise tubing, such as plastic tubing.

During operation, the exchangeable separation insert 6, arranged in a rotatable member, is brought into rotation around the axis 20 of rotation. Liquid feed mixture to be separated is supplied via the first fluid connection 96 arranged in the first stationary portion 86 and guiding channels 106 into the separation space 88. The liquid feed mixture to be separated is guided along an axially upwardly path into the separation space 88. Due to a density difference the liquid feed mixture is separated into a liquid light phase and a liquid heavy phase. This separation is facilitated by the interspaces between the separation discs 92 of the stack 90 fitted in the separation space 88. The heavy phase may comprise particles, such as e.g. cells. The heavy phase may comprise a concentrated mixture of light phase and particles.

The separated heavy phase is collected from the periphery of the separation space 88 via outlet conduit 102 and is forced out of the rotor casing 82 to the second fluid connection 94 arranged in the second stationary portion 84. Separated light phase is forced radially inwardly through the stack 90 of separation discs 92 and led out of the rotor casing 82 to the third fluid connection 98 arranged in the first stationary portion 86. Consequently, in this embodiment, the liquid feed mixture is supplied at a lower axial end of the exchangeable separation insert 6, the separated light phase is discharged at the lower axial end, and the separated heavy phase is discharged at the upper axial end of the exchangeable separation insert 6.

The exchangeable separation insert 6 comprises a ring member 124 which extends concentrically with the axis 20 of rotation at the first axial end portion 120. The ring member 124 is axially displaceable between a first position, shown in FIG. 2, in which the ring member 124 abuts radially against the rotor casing 82 and abuts radially against the first stationary portion 86, and a second position, in which the ring member 124 abuts radially against the rotor casing 82 only, see FIG. 2a or against the first stationary portion 86 only, see FIG. 2b.

Figure 2A:
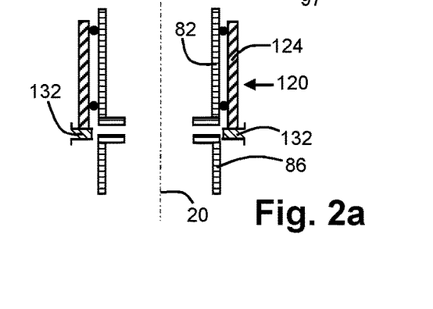
Figure 2B:
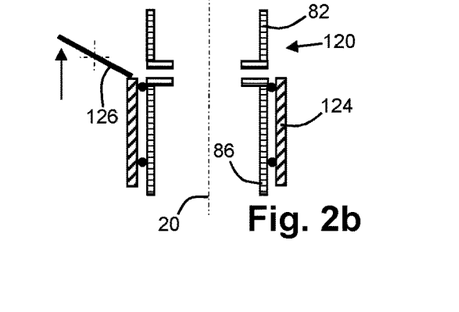

Namely, FIGS. 2a and 2b schematically illustrate cross sections through part of the first axial end portion 120 of the rotor casing 82 and part of the first stationary portion 86. In FIGS. 2a and 2b alternative second positions of the ring member 122 are shown.

According to a first embodiment, shown in FIG. 2a, in its second position, the ring member 124 abuts radially against the rotor casing 82 only. In accordance with the first embodiment, the axial displacement from the first to the second position of the ring member 124 may be achieved when the exchangeable separation insert 6 is installed in the modular centrifugal separator. More specifically, as the exchangeable separation insert 6 is arranged in a rotatable member of the modular centrifugal separator, the ring member 124 abuts against a protrusion 132 of the rotatable member. The ring member 124 abuts against the protrusion 132 before the exchangeable separation insert 6 is fully inserted into the rotatable member, with the ring member 124 arranged in its first position. Inserting the exchangeable separation insert 6 fully into the rotatable member, the protrusion 132 prevents the ring member 124 from being further inserted into the rotatable member. Thus, the ring member 124 is axially displaced in relation to the rotor casing 82 to its second position. In FIG. 2, the ring member 124 is shown in its first position abutting against the protrusion 132 of the rotatable member. In FIG. 2a, the ring member 124 is shown in its second position abutting against the protrusion 132. See also below under the discussions related to FIGS. 3 and 4.

According to a second embodiment, shown in FIG. 2b, in its second position, the ring member 124 abuts radially against the first stationary portion 86 only. In accordance with the second embodiment, the axial displacement from the first to the second position of the ring member 124 may be achieved by means of a lever 126 being pushed against the ring member 124 after the exchangeable separation insert 6 has been installed in the modular centrifugal separator. In these second embodiments, the inside of the rotatable member of the modular centrifugal separator is not provided with the protrusion 132 discussed inter alia with reference to FIGS. 2 and 2a.

In its first position, the ring member 124 prevents a sterile environment within the exchangeable separation insert 6 from being contaminated via the boundary between the rotor casing 82 and the first stationary portion 86 while the exchangeable separation insert 6 is handled prior to and during mounting thereof in the modular centrifugal separator. Moreover, in the first position the ring member may contribute to hold the rotor casing 82 and the first stationary portion 86 together when the exchangeable separation insert 6 is handled.

The rotor casing 82 is rotatable in relation to the first stationary portion 86 when the ring member 124 is positioned in the second position. Thus, in the second position of the ring member 124, the rotor casing 82 is released from the first stationary portion 86.

Suitably, the ring member 124 is arranged in sealing abutment with the rotor casing 82 and with the first stationary portion 86 when the ring member 124 is positioned in the first position. Accordingly, the ring member 124 contributes to maintaining a sterile environment inside the rotor casing 82 and the first stationary portion 86 by sealing off the boundary area between the rotor casing 82 and the first stationary portion 86 while the ring member 124 is positioned in the first position. The sealing abutment may be achieved e.g. with lip seals, or O-rings, as shown in FIG. 2-2b.

The exchangeable separation insert 6 comprises a sleeve member 128. The sleeve member 128 is arranged in a setup position in sealing abutment with the rotor casing 82 and the second stationary portion 84, see FIG. 2. The sleeve member 128 is removable from the setup position for permitting the rotor casing 82 to rotate in relation to the second stationary portion 84.

In its setup position, the sleeve member 128 contributes to maintaining a sterile environment inside the rotor casing 82 and the second stationary portion 84. Also, the sleeve member 128 holds the second stationary portion 84 in place at the rotor casing 82 during handling of the exchangeable separation insert 6. Suitably, after the rotor casing 82 has been mounted in the modular centrifugal separator, the sleeve member 128 is removed from the setup position. Thus, during use of the modular centrifugal separator, the rotor casing 82 is rotatable in in relation to the second stationary portion 84.

According to embodiments, the sleeve member 128 may be resilient. In this manner, the sleeve member 128 may be easily removed from its setup position without damaging the rotor casing 82 or the second stationary portion 84. Moreover, a resilient sleeve member 128 may seal tightly against the rotor casing 82 and the second stationary portion 84 when arranged in its setup position.

According to embodiments, the sleeve member 128 in the setup position seals radially against the rotor casing 82 and radially against the second stationary portion 84. In this manner, the sleeve member 128 may be removed from its setup position in an axial direction. That is, when the exchangeable separation insert 6 is positioned as shown in FIG. 2, the sleeve member 128 is removed from its setup position upwardly substantially in parallel with the axis 20 of rotation.

The first stationary portion 86 comprises an outer threaded portion 130. The outer threaded portion 130 is configured to engage with a correspondingly inner threaded portion. The inner threaded portion may be provided as part of an engagement member provided at the stationary frame of the modular centrifugal separator. Thus, the first stationary portion 86 may be fixed in relation to the stationary frame, see further below with reference to FIG. 4.

Figure 3:
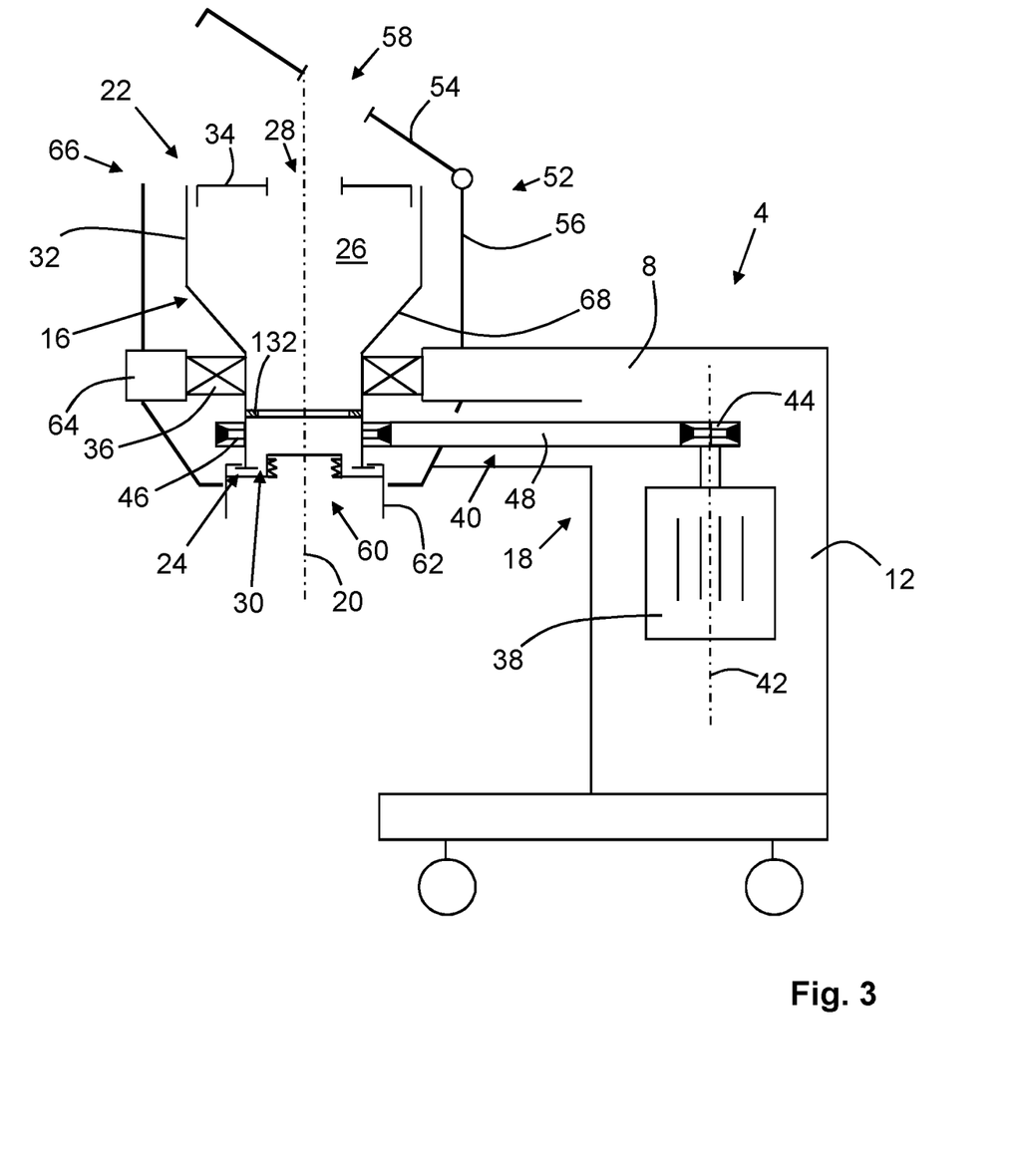

FIG. 3 schematically illustrates a cross section through the base unit 4 of the modular centrifugal separator 2 of FIG. 1. That is, in FIG. 3 the exchangeable separation insert has been omitted.

As mentioned above, the base unit 4 comprises the stationary frame 8, the rotatable member 16, and the drive unit 18. The rotatable member 16 is arranged in the stationary frame 8 and is configured to rotate about an axis 20 of rotation. The drive unit 18 is configured for rotating the rotatable member 16 about the axis 20 of rotation.

Seen along the axis 20 of rotation, the rotatable member 16 has a first axial end 24 and a second axial end 22. The rotatable member 16 delimits an inner space 26 at least in a radial direction. The radial direction extends perpendicularly to the axis 20 of rotation. The inner space 26 is configured for receiving at least one part of the exchangeable separation insert 6 therein, see further below with reference to FIG. 4.

The rotatable member 16 is provided with a first opening 30 at the first axial end 24. The rotatable member 16 further is provided with a second opening 28 at the second axial end 22. Each of the first and second openings 30, 28 forms a through hole in the rotatable member 16. Thus, the inner space 26 is accessible via each of the first and second openings 30, 28. Accordingly, the first and second openings 30, 28 are configured for fluid connections of the exchangeable separation insert to extend therethrough. See further below with reference to FIG. 4.

In these embodiments, the rotatable member 16 comprises a rotor body 32 and a cap 34. The cap 34 is releasably engaged with the rotor body 32. The cap 34 may for instance be releasably engaged with the rotor body 32 by means of threads, a bayonet coupling, screws, wingnuts, or any other suitable engagement arrangement. When the cap 34 is released from the rotor body 32, access to the inner space 26 is provided. When access to the inner space 26 is provided, an exchangeable separation insert may be mounted in the inner space 26. Similarly, when access to the inner space 26 is provided, an exchangeable separation insert may be removed from the inner space 26. Thus, a used exchangeable separation insert may be replaced with a new exchangeable separation insert when the cap 34 has been released from the rotor body 32.

The cap 34 may be arranged in a region of the second axial end 22 of the rotor body 32. Accordingly, the second opening 28 of the rotatable member 16 is arranged in the cap 34. As mentioned above, a fluid connection of the exchangeable separation insert may extend through the second opening 28.

The base unit 4 comprises at least one bearing 36. The rotatable member 16 is journalled in the stationary frame 8 via the at least one bearing 36. Accordingly, the rotatable member 16 as such is journalled in the stationary frame 8. Also, the rotatable member 16 may be supported in the stationary frame 8 via the at least one bearing 36. Accordingly, the rotatable member 16 is not indirectly journalled via a spindle or shaft as in prior art centrifugal separators comprising an exchangeable separation insert.

The at least one bearing 36 may for instance be one single ball bearing which supports both radial and axial forces. Alternatively, the at least one bearing 36 may comprise e.g. two bearings, for instance one which primarily supports radial forces and one which primarily supports axial forces.

The at least one bearing 36 is arranged at an axial position along the axis 20 of rotation such that the at least one bearing 36 extends around a portion of the inner space 26 delimited by the rotatable member 16. Since during use of the modular centrifugal separator the exchangeable separation insert is arranged in the inner space 26, the rotatable member 16 is supported in an axial position where the exchangeable separation insert also is positioned. Thus, the at least one bearing 36 provides reliable support of the rotatable member 16.

According to some embodiments, the at least one bearing 36 may have an inner diameter of at least –80 mm. In this manner, the at least one bearing 36 is sized such that a portion of the rotatable member 16 where it delimits the inner space 26 may fit within the at least one bearing 36. Also, in this manner, the at least one bearing 36 is sized such that, seen along the axis 20 of the rotational, the first opening 30 of the rotatable member 16 may fit within the at least one bearing 36. According to some embodiments, the at least one bearing 36 may have an inner diameter within a range of 80-150 mm. According to one non-limiting example the at least one bearing 36 may have an inner diameter of approximately 120 mm. Such large bearings are not common in centrifugal separators, in particular not in centrifugal separators having separation discs of the size discussed below. Since the bearing 36 is arranged as described above in the base unit 4, the large bearing 36 inter alia permits part of the exchangeable separation insert to fit within the at least one bearing 36.

The drive unit 18 comprises an electric motor 38, and a transmission 40 arranged between the electric motor 38 and the rotatable member 16. The transmission 40 provides for the electric motor 38 to be arranged axially beside the rotatable member 16. That is, an axis 42 of rotation of the electric motor 38 extends substantially in parallel with the axis 20 of rotation of the rotatable member 16. Since the electric motor 38 is arranged axially beside the rotatable member 16, access inter alia to both the first and second axial ends 24, 22 of the rotatable member 16 may be provided. That is, access to neither of the first and second axial ends 24, 22 is blocked by the electric motor 38.

In the shown embodiments, the transmission 40 is a belt drive comprising a first pulley 44 arranged on the electric motor 38, a second pulley 46 arranged on the rotatable member 16, and a belt 48 extending between the first and second pullies 44, 46. Alternatively, the transmission may be a gear transmission comprising cog wheels, or any other suitable transmission for transferring torque from the electric motor 38 to the rotatable member 16.

In the shown embodiments, the stationary frame 8 comprises a vertical member 12. The electric motor 38 is arranged at least partially inside the vertical member 12. In this manner, the electric motor at 38 is protectively arranged within the stationary frame 8. A user of the modular centrifugal separator will not risk coming into contact with rotating parts of, or at, the electric motor 38. Similarly, the belt 48 may be arranged at least partly inside the stationary frame 8 in order to prevent a user of the modular centrifugal separator from coming into contact therewith.

The stationary frame 8 comprises a housing 52. The rotatable member 16 is arranged inside the housing 52. The housing 52 comprises a lid 54, which is pivotably or removably connected to a first housing portion 56 of the housing 52. The lid 54 is provided with a third opening 58. The third opening 58 forms a through hole in the lid 54.

In an open position of the lid 54, access is provided to the rotatable member 16 inside the housing 52, e.g. for exchange of the exchangeable separation insert. Thus, in order to remove and/or position an exchangeable separation insert inside the rotatable member 16, the lid 54 is moved to its open position and the cap 34 of the rotatable member 16 is released from the rotor body 32. Once the exchangeable separation insert has been positioned inside the inner space 26 of the rotatable member 16 the cap 34 is again engaged with the rotor body 32. Thereafter the lid 54 is moved to a closed position.

In the closed position of the lid 54 the third opening 58 is configured for a fluid connection of the exchangeable separation insert to extend therethrough. During use of the modular centrifugal separator the lid the 54 is arranged in its closed position. Thus, the rotatable member 16 cannot be accessed by a user of the modular centrifugal separator. The third opening 58 provides for one of the fluid connections of the exchangeable separation insert to extend therethrough and permit fluid to pass to, or pass from, the exchangeable separation insert at the second axial end 22 of the rotatable member 16.

A fourth opening 60 is provided opposite to the lid 54. The fourth opening 60 is configured for a further fluid connection of the exchangeable separation insert to extend therethrough. Thus, the further fluid connection may extend from the housing 52 at the first axial end 24 of the rotatable member 16.

The fourth opening 60 may be provided in the housing 52, and/or in the stationary frame 8, and/or in an engagement member 62 arranged at the first axial end 24. In any case, the fourth opening 60 forms a through hole thus, permitting the further fluid connection of the exchangeable separation insert to extend therethrough.

In these embodiments, the base unit 4 comprises an engagement member 62. The engagement member 62 is arranged at the fourth opening 60. The engagement member 62 is configured to engage with a portion of the exchangeable separation insert, see further below with reference to FIG. 4.

The stationary frame 8 comprises a protruding member 64. The housing 52 is connected to the protruding member 64. Thus, access is provided to the housing 52 and also to the rotatable member 16 arranged in the housing 52. The housing 52 is connected to the protruding member 64 such that access is provided at least to one end 66 of the housing 52 along the axis 20 of rotation. Suitably, the housing 52 is connected to the protruding member 64 in a manner such that access is provided to that end of the housing 52 where the lid 54 is arranged. Thus, a user may access an inside of the housing 52, e.g. for exchanging the exchangeable separation insert in the rotatable member 16. Moreover, if access is provided at opposite ends of the housing 52 along the axis 20 of rotation, the user will be able to install the first and second fluid connections of the exchangeable separation insert through the first, second, third, and fourth openings 28, 30, 58, 60.

The rotatable member 16 is journalled inside the housing 52 of the stationary frame 8. That is, the bearing 36 in which the rotatable member 16 is journalled is arranged within the housing 52. The housing 52 may be suspended in the protruding member 64 via at least one resilient connector (not shown) to reduce negative effects on the modular centrifugal separator when the rotatable member 16 together with the rotor casing of the exchangeable separation insert passes the critical speed during operation of the modular centrifugal separator.

The rotatable member 16 comprises a frustoconical wall member 68 having an imaginary apex in a region of the first axial end 24. The frustoconical wall member 68 delimits a portion of the inner space 26. When positioned in the inner space 26, an exchangeable separation insert having a conical or frustoconical shape is supported by the frustoconical wall member 68. The frustoconical wall member 68 forms part of the rotor body 32.

The rotatable member 16 comprises a protrusion 132. The protrusion 132 is provided at an inner surface of the rotatable member 16. The protrusion 132 is arranged in an axial position of the rotatable member 16 such that a ring member of the exchangeable separation insert will abut against the protrusion 132. More specifically, the protrusion 132 will abut against the ring member when in its first position. As the exchangeable separation insert is moved fully into the rotatable member 16 the ring member is moved into its second position. See above with reference to FIG. 2a.

In these embodiments, the protrusion 132 forms a ridge extending circumferentially along the inner surface of the rotatable member 16. The protrusion 132 may have any suitable shape for abutting against the ring member of the exchangeable separation insert. For instance, the protrusion may form a discrete element protruding from the inner surface of the rotatable member 16. Such a discrete element may be complemented with one or more similar discrete elements protruding from the inner surface of the rotatable member 16.

Figure 4:
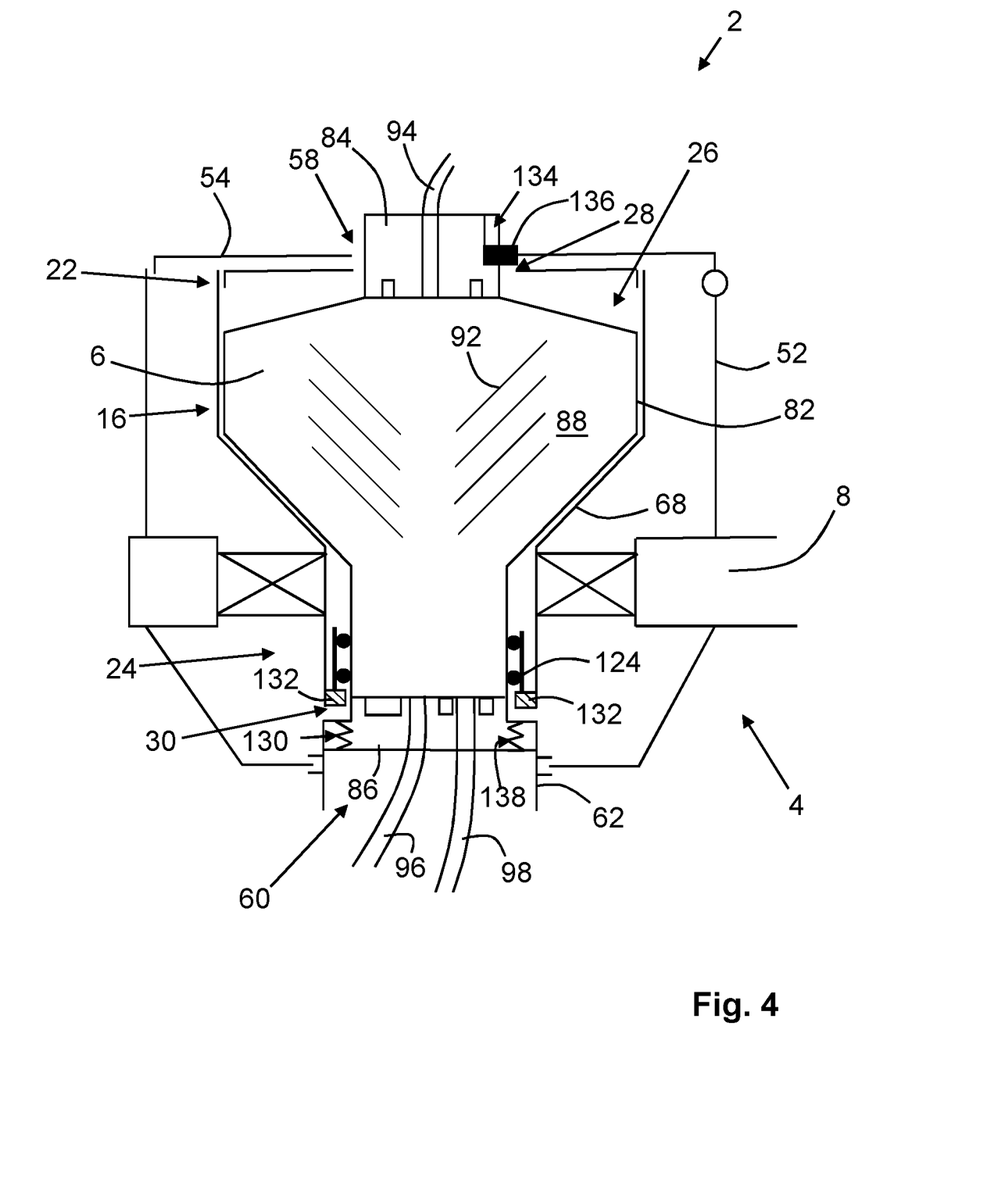

FIG. 4 schematically illustrates a cross section through a portion of a modular centrifugal separator 2. More specifically, FIG. 4 shows a cross section through a housing 52, a rotatable member 16, and an exchangeable separation insert 6 of the modular centrifugal separator 2. The modular centrifugal separator 2 may be a modular centrifugal separator 2 as discussed above in connection with FIGS. 1-3. The exchangeable separation insert 6 may be an exchangeable separation insert 6 as discussed above in connection with FIGS. 2 and 2a. Accordingly, in the following, reference is also made to FIGS. 1-3.

In FIG. 4 the exchangeable separation insert 6 is shown mounted in the base unit 4. Part of the exchangeable separation insert 6 is engaged inside the rotatable member 16. More specifically, the rotor casing 82 of the exchangeable separation insert 6 is engaged in the inner space 26 of the rotatable member 16 with the second fluid connection 94 of the exchangeable separation insert 6 extending through the second opening 28 of the rotatable member 16 and a first fluid connection 96 of the exchangeable separation insert 6 extending through the first opening 30 of the rotatable member 16. In these embodiments, also the third fluid connection 98 extends through the first opening 30.

The rotor casing 82 may be engaged inside the rotatable member 16 in a number of different ways. For instance, the cap 34 when engaged with the rotor body 32, may engage the rotor casing 82, an inside of the rotatable member 16 may be provided with protrusions and the rotor casing 82 may be provided with corresponding recesses, etc.

Part of the first stationary portion 86 extends through the first opening 30. Thus, at the first axial end 24 of the rotor casing 82, at least part of the first stationary portion 86 is arranged outside the rotatable member 16. Accordingly, the first stationary portion 86 may be engaged with the stationary frame 8 to ensure that the first stationary portion 86 remains stationary during operation of the modular centrifugal separator 2.

Part of the second stationary portion 84 extends through the second opening 28. Thus, at the second axial end 22 of the rotor casing 82, at least part of the second stationary portion 84 is arranged outside the rotatable member 16. Accordingly, the second stationary portion 84 may be engaged with the stationary frame 8 to ensure that the second stationary portion 84 remains stationary during operation of the modular centrifugal separator 2.

The first and second openings 30, 28 at opposite axial ends 24, 22 of the rotatable member 16 provide for easy mounting of the exchangeable separation insert 6 in the rotatable member 16 with the first and second fluid connections 96, 94 extending through respective of the first and second openings 30, 28.

Thus, the first fluid connection 96 extending through the first opening 30 may extend to equipment external of the modular centrifugal separator 2. Similarly, the second fluid connection 94 extending through the second opening 28 may extend to equipment external of the modular centrifugal separator 2. Accordingly, the first and second fluid connections 96, 94 may be connected to such external equipment.

The fluid connections 94, 96, 98 of the exchangeable separation insert 6 extend out of the housing 52. The second fluid connection 94 extends through the third opening 58 of the housing 52. Also, at least part of the second stationary portion 84 extends through the third opening 58. The first fluid connection 96 extends through a fourth opening 60. As mentioned above, the fourth opening 60 may be provided in the housing 52, or alternatively, in a different portion of the stationary frame 8 of the modular centrifugal separator 2. In these embodiments, also the third fluid connection 98 extends through the fourth opening 60.

As mentioned above in connection with FIG. 3, the third opening 58 may be provided in a lid 54 of the housing 52. The lid 54 is configured to engage with a portion of the exchangeable separation insert 6. More specifically, the lid 54 is configured to engage with the second stationary portion 84. Thus, the second stationary portion 84 is fixedly engaged in the stationary frame 8. Accordingly, the second stationary portion 84 is maintained in a predefined position during use of the modular centrifugal separator. Hence, also the second fluid connection 94 is rotationally fixed during use of the modular centrifugal separator 2.

The purpose of the engagement between the lid 54 and the second stationary portion 84 is to prevent the second stationary portion 84 from rotating during use of the modular centrifugal separator 2. Moreover, the engagement between the lid 54 and the second stationary portion 84 may contribute to positioning the exchangeable separation insert 6 in a correct axial position. For instance, in the closed position of the lid 54, the lid may press the second stationary portion 84 towards the rotor casing 82, such that the seals within the exchangeable separation insert 6 provide their intended sealing function.

The lid 54 may engage with the second stationary portion 84 in a number of different ways. For instance, the second stationary portion 84 may be provided with a radial recess 134 and the lid 54 may be provided with a protrusion 136 extending into the radial recess 134. Alternatively, or additionally, e.g. the second stationary portion 84 may be provided with an axial flange and the lid 54 may abut against the axial flange.

According to the illustrated embodiments, the modular centrifugal separator 2 may comprise an engagement member 62 rotatably connected to the stationary frame 8. The exchangeable separation insert 6 may be an exchangeable separation insert 6 wherein the first stationary portion 86 comprises an outer threaded portion 130. The engagement member 62 comprises an inner threaded portion 138 configured to engage with the outer threaded portion 130 of the first stationary portion 86.

As mentioned above in connection with FIG. 3, an engagement member 62 is arranged at the fourth opening 60.

More specifically, the fourth opening 60 extends through the engagement member 62. The engagement member 62 is configured to engage with a portion of the exchangeable separation insert 6. More specifically, the engagement member 62 is configured to engage with the first stationary portion 86 of the exchangeable separation insert 6. When engaged with the first stationary portion 86, the engagement member 62 and the first stationary portion 86 are fixed in relation to the stationary frame 8, i.e. the first stationary portion 86 is fixedly engaged with the stationary frame 8.

In these embodiments, the engagement member 62 comprises an inner threaded portion 138 and the first stationary portion 86 comprises the outer threaded portion 130, as discussed above with reference to FIG. 2. Thus, the engagement member 62 is threadedly engaged with the first stationary portion 86. According to alternative embodiments, e.g. a bayonet coupling may be provided between the engagement member 62 and the first stationary portion 86.

The rotatable member 16 comprises a frustoconical wall member 68 having an imaginary apex in a region of the first axial end 24 of the rotatable member 16. A portion of the exchangeable separation insert 6 has a conical or frustoconical shape. The conical or frustoconical portion of the exchangeable separation insert 6 is supported by the frustoconical wall member 68. The conical or frustoconical portion of the exchangeable separation insert 6 may be derived from the frustoconical shape of the separation discs 92 arranged in the separation space 88 of the rotor casing 82.

When the exchangeable separation insert 6 is mounted in the modular centrifugal separator 2, and the modular centrifugal separator is ready for use, as shown in FIG. 4, the ring member 124 of the exchangeable separation insert 6 is arranged in its second position as discussed above, e.g. in connection with FIGS. 2a and 2b. Thus, rotor casing 82 is rotatable together with the rotatable member 16 by the drive unit of the modular centrifugal separator 2.

In the illustrated embodiments, and as also discussed above with reference to FIGS. 2 and 2a, the rotatable member 16 comprises a protrusion 132. The ring member 124 of the exchangeable separation insert 6 abuts against the protrusion 132. As discussed above, since the ring member 124 abuts against the protrusion 132, the ring member 124 is axially displaced from a first position to a second position as the exchangeable separation insert 6 is positioned in the rotatable member 16 and the frame 8 of the modular centrifugal separator 2.

Figure 5:
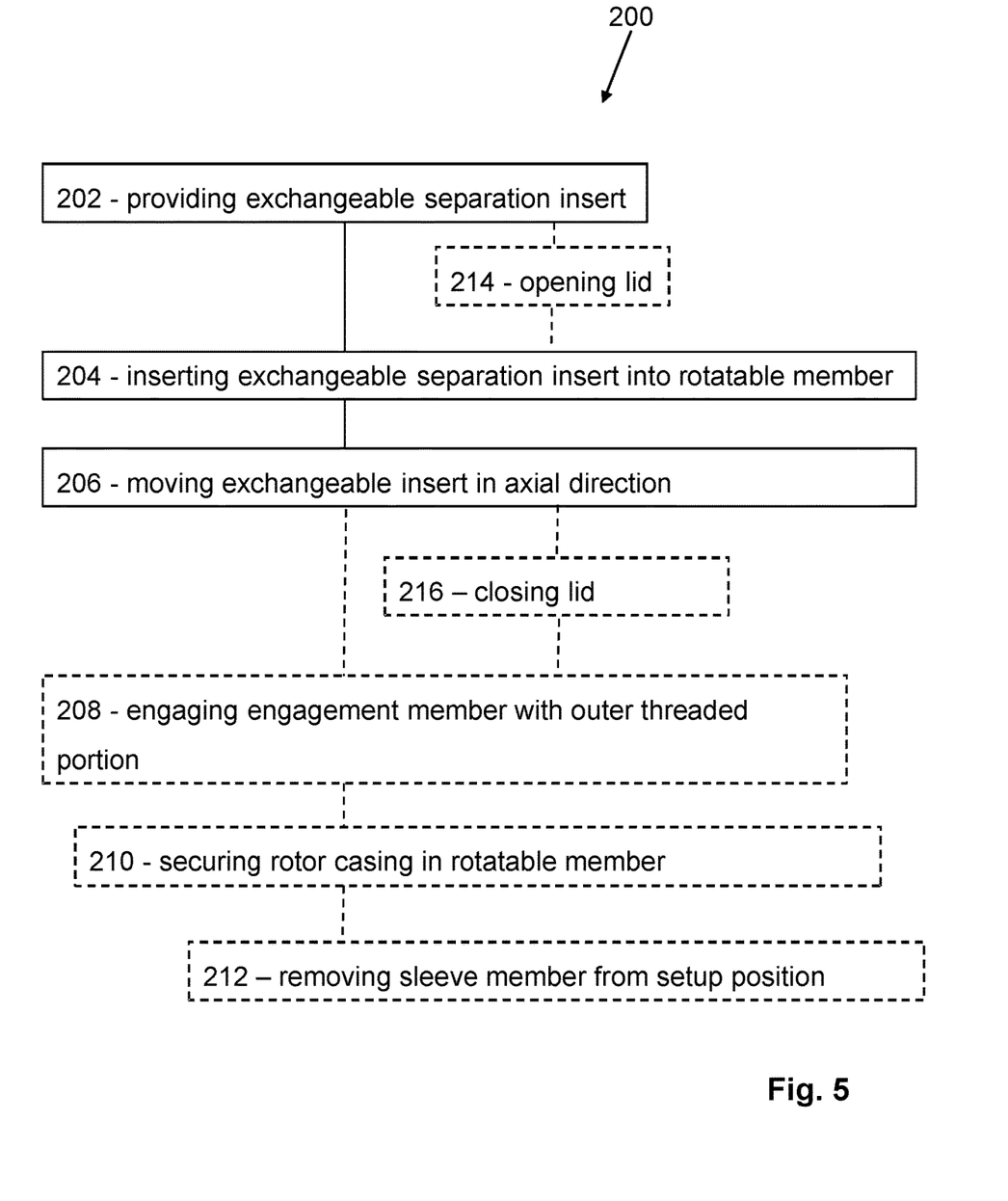
FIG. 5 illustrates a method of mounting an exchangeable insert in a modular centrifugal separator.

FIG. 5 illustrates a method 200 of mounting an exchangeable insert in a modular centrifugal separator. The modular centrifugal separator may be a modular centrifugal separator 2 according to any one of aspects and/or embodiments discussed herein and comprises an exchangeable separation insert 6 according to any one of aspects and/or embodiments discussed herein. Accordingly, in the following reference is also made to FIGS. 1-4.

The method 200 comprises steps of:
providing 202 an exchangeable separation insert 6 according to any one of aspects and/or embodiments discussed herein,
inserting 204 the exchangeable separation insert 6 into the rotatable member 16 to a position in which the ring member 124 abuts against a protrusion 132 within the rotatable member 124, and
moving 206 the exchangeable insert 6 in an axial direction of the rotatable member 16 further into the rotatable member 16, thus pushing the ring member 124 from its first position to its second position.

According to embodiments, wherein the modular centrifugal separator 2 comprises the engagement member 62 with the inner threaded portion 138 configured to engage with the outer threaded portion 130 of the first stationary portion 86 of the exchangeable separation insert 6, the method 200 may comprise a step of:
engaging 208 the engagement member 62 of the stationary frame 8 with the outer threaded portion 130 of the first stationary portion 86 of the exchangeable separation insert 6. In this manner, the first stationary portion 86 may be fixed in relation to the stationary frame 8, as discussed above e.g. in connection with FIG. 4.

According to embodiments, the method 200 may comprise a step of:
securing 210 the rotor casing 82 of the exchangeable separation insert 6 in the rotatable member 16 by engaging a cap 34 of the rotatable member 16 with a rotor body 32 of the rotatable member 16. In this manner, the rotor casing 82 may be easily secured in the modular centrifugal separator 2, see further above with reference to FIGS. 3 and 4.

According to embodiments, wherein the modular centrifugal separator 2 comprises a sleeve member 128 arranged in a setup position in sealing abutment with the rotor casing 82 and the second stationary portion 84, the method 200 may comprise a step of:
removing 212 the sleeve member 128 from its setup position. See further above with reference to FIG. 2.

The order in which the steps 208, 210, 212 are performed may differ from the order shown in FIG. 5.

According to embodiments, wherein the modular centrifugal separator 2 comprises a stationary frame 8 with a housing 52 comprising a lid 54, the step of inserting 204 the exchangeable separation insert 6 into the rotatable member 16 may be preceded by a step of:
opening 214 the lid 54 of the housing 52, and the step of moving 206 the exchangeable insert 6 in an axial direction of the rotatable member 16 may be succeeded by a step of:
closing 216 the lid 54 and thereby pressing the second stationary portion 84 towards the rotor casing 82. In this manner, seals of the exchangeable separation insert 6 may be arranged in positions adequate for performing their intended sealing function during operation of the modular centrifugal separator 2.

It is to be understood that the foregoing is illustrative of various example embodiments and that the invention is defined only by the appended claims. A person skilled in the art will realize that the example embodiments may be modified, and that different features of the example embodiments may be combined to create embodiments other than those described herein, without departing from the scope of the invention, as defined by the appended claims.

The invention claimed is:

1. An exchangeable separation insert of a modular centrifugal separator, the exchangeable separation insert comprising:
a rotor casing rotatable about an axis of rotation and having a first axial end portion and a second axial end portion, and
a first stationary portion provided with a first conduit portion,
wherein the first stationary portion abuts against the rotor casing at the first axial end portion,
wherein the rotor casing delimits a separation space, wherein the exchangeable separation insert comprises frustoconical separation discs arranged in the separation space, wherein the first conduit portion is fluidly connected with the separation space, wherein the exchangeable separation insert comprises a ring member which extends concentrically with the axis of rotation at the first axial end portion, and wherein the ring member is axially displaceable between a first position, in which the ring member abuts radially against the rotor casing and abuts radially against the first stationary portion, and a second position, in which the ring member abuts radially against the rotor casing only or against the first stationary portion only.

2. The exchangeable separation insert according to claim 1, wherein the ring member is arranged in sealing abutment with the rotor casing and with the first stationary portion when the ring member is positioned in the first position.

3. The exchangeable separation insert according to claim 1, wherein the rotor casing is rotatable in relation to the first stationary portion when the ring member is positioned in the second position.

4. The exchangeable separation insert according to claim 1, comprising a first sealing member arranged between the first stationary portion and the rotor casing, wherein the first sealing member seals a transition of the first conduit portion to the rotor casing.

5. The exchangeable separation insert according to claim 4, wherein the first sealing member is fixedly arranged in the first stationary portion and comprises a first annular sealing surface abutting against a first opposite sealing surface arranged at the rotor casing.

6. The exchangeable separation insert according to claim 1, comprising a second stationary portion provided with a second conduit portion, wherein the second stationary portion abuts against the rotor casing at the second axial end portion, and wherein the second conduit portion is fluidly connected with the separation space.

7. The exchangeable separation insert according to claim 6, comprising a second sealing member arranged between the second stationary portion and the rotor casing, wherein the second sealing member seals a transition of the second conduit portion to the rotor casing.

8. The exchangeable separation insert according to claim 7, wherein the second sealing member is fixedly arranged in the second stationary portion and comprises a second annular sealing surface abutting against a second opposite sealing surface arranged at the rotor casing.

9. The exchangeable separation insert according to claim 1, comprising a sleeve member and a second stationary portion provided with a second conduit portion, wherein the sleeve member is arranged in a setup position in sealing abutment with the rotor casing and the second stationary portion, and wherein the sleeve member is removable from the setup position for permitting the rotor casing to rotate in relation to the second stationary portion.

10. The exchangeable separation insert according to claim 9, wherein the sleeve member is resilient.

11. The exchangeable separation insert according to claim 9, wherein the sleeve member in the setup position seals radially against the rotor casing and radially against the second stationary portion.

12. The exchangeable separation insert according to claim 1, wherein the first stationary portion is provided with a third conduit portion which is fluidly connected with the separation space.

13. The exchangeable separation insert according to claim 12, comprising a third sealing member arranged between the first stationary portion and the rotor casing, wherein the third sealing member seals a transition of the third conduit portion to the rotor casing.

14. The exchangeable separation insert according to claim 13, wherein the third sealing member is fixedly arranged in the first stationary portion and comprises a third annular sealing surface abutting against a third opposite sealing surface arranged at the rotor casing.

15. The exchangeable separation insert according to claim 1, wherein the first stationary portion comprises an outer threaded portion.

16. A modular centrifugal separator comprising:

a stationary frame, a rotatable member, a drive unit for rotating the rotatable member, and the exchangeable separation insert according to claim 1, wherein the rotor casing is engaged inside the rotatable member, and the first stationary portion is fixedly engaged with the stationary frame, and wherein the ring member is arranged in the second position.

17. The modular centrifugal separator according to claim 16, wherein the rotatable member has a first axial end and a second axial end, wherein the rotatable member is provided with a first opening at the first axial end, and wherein part of the exchangeable separation insert extends through the first opening.

18. The modular centrifugal separator according to claim 17, wherein the exchangeable separation insert comprises a second stationary portion provided with a second conduit portion, wherein the second stationary portion abuts against the rotor casing at the second axial end portion, wherein the second conduit portion is fluidly connected with the separation space, and wherein the second stationary portion is fixedly engaged in the stationary frame.

19. The modular centrifugal separator according to claim 18, wherein the rotatable member is provided with a second opening at the second axial end, and wherein part of the exchangeable separation insert extends through the second opening.

20. The modular centrifugal separator according to claim 16, comprising an engagement member rotatably connected to the stationary frame, wherein the exchangeable separation insert is an exchangeable separation insert wherein the first stationary portion comprises an outer threaded portion, and wherein the engagement member comprises an inner threaded portion configured to engage with the outer threaded portion.

21. The modular centrifugal separator according to claim 16, wherein the rotatable member comprises a protrusion, and wherein the ring member of the exchangeable separation insert abuts against the protrusion.

22. The modular centrifugal separator according to claim 18, wherein the stationary frame comprises a housing, wherein the rotatable member is arranged inside the housing, wherein the housing comprises a lid provided with a third opening, wherein, in an open position of the lid, access is provided to the rotatable member for exchange of the exchangeable separation insert, and wherein, in a closed position of the lid, the third opening is configured for a fluid connection of the exchangeable separation insert to extend therethrough.

23. The modular centrifugal separator according to claim 22, wherein the lid is configured to engage with the second stationary portion of the exchangeable separation insert.

24. The modular centrifugal separator according to claim 22, wherein in the closed position of the lid, the lid presses the second stationary portion towards the rotor casing.

25. A method of mounting an exchangeable insert in the modular centrifugal separator according to claim 16, comprising steps of:

providing the exchangeable separation insert, inserting the exchangeable separation insert into the rotatable member to a position in which the ring member abuts against a protrusion within the rotatable member, moving the exchangeable insert in an axial direction of the rotatable member further into the rotatable member, thus pushing the ring member from the first position thereof to the second position thereof.

26. The method according to claim 25, wherein the modular centrifugal separator comprises an engagement member rotatably connected to the stationary frame, wherein the exchangeable separation insert is an exchangeable separation insert wherein the first stationary portion comprises an outer threaded portion, wherein the engagement member comprises an inner threaded portion configured to engage with the outer threaded portion, and wherein the method comprises a step of:

engaging the engagement member of the stationary frame with the outer threaded portion of the first stationary portion of the exchangeable separation insert.

27. The method according to claim 25, comprising a step of:

securing the rotor casing of the exchangeable separation insert in the rotatable member by engaging a cap of the rotatable member with a rotor body of the rotatable member.

28. The method according to claim 25, wherein the modular centrifugal separator comprises a sleeve member, wherein the exchangeable separation insert includes a second stationary portion provided with a second conduit portion, wherein the sleeve member is arranged in a setup position in sealing abutment with the rotor casing and the second stationary portion, wherein the sleeve member is removable from the setup position for permitting the rotor casing to rotate in relation to the second stationary portion, and wherein the method comprises a step of:

removing the sleeve member from a setup position thereof.

29. The method according to claim 25, wherein the stationary frame comprises a housing, wherein the exchangeable separation insert includes a second stationary portion provided with a second conduit portion, wherein the rotatable member is arranged inside the housing, wherein the housing comprises a lid provided with a third opening, wherein, in an open position of the lid, access is provided to the rotatable member for exchange of the exchangeable separation insert, wherein, in a closed position of the lid, the third opening is configured for a fluid connection of the exchangeable separation insert to extend therethrough, and wherein the step of inserting the exchangeable separation insert into the rotatable member is preceded by a step of:

opening the lid of the housing, and wherein the step of moving the exchangeable insert in an axial direction of the rotatable member is succeeded by a step of:

closing the lid and thereby pushing the second stationary portion towards the rotor casing.

* * * * *